United States Patent
Gunderson (10) Patent No.: US 7,473,271 B2
(45) Date of Patent: Jan. 6, 2009

(54) STENT DELIVERY SYSTEM WITH SECUREMENT AND DEPLOYMENT ACCURACY

(75) Inventor: Richard Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 716 days.

(21) Appl. No.: 10/411,645

(22) Filed: Apr. 11, 2003

(65) Prior Publication Data

US 2004/0204749 A1 Oct. 14, 2004

(51) Int. Cl.
*A61F 2/06* (2006.01)
(52) U.S. Cl. .................................... 623/1.12
(58) Field of Classification Search ............... 623/1.11, 623/1.12, 1.2, 1.34, 1.23; 606/108, 191–198, 606/1

See application file for complete search history.

(56) References Cited

U.S. PATENT DOCUMENTS

| | | | |
|---|---|---|---|
| 4,503,569 A | 3/1985 | Dotter | 3/1.4 |
| 4,733,665 A | 3/1988 | Palmaz | 128/343 |
| 4,950,227 A | 8/1990 | Savin et al. | |
| 4,990,151 A | 2/1991 | Wallsten | |
| 5,026,377 A | 6/1991 | Burton et al. | 606/108 |
| 5,290,295 A | 3/1994 | Querals et al. | |
| 5,409,495 A | 4/1995 | Osborn | |
| 5,484,444 A | 1/1996 | Braunschweiler et al. | 606/108 |
| 5,534,007 A | 7/1996 | St. Germain et al. | |
| 5,645,559 A | 7/1997 | Hachtman et al. | |
| 5,693,066 A | 12/1997 | Rupp et al. | |
| 5,702,418 A | 12/1997 | Ravenscroft | |
| 5,707,376 A | 1/1998 | Kavteladze et al. | |
| 5,709,703 A | 1/1998 | Lukic et al. | 606/198 |
| 5,725,549 A | 3/1998 | Lam | 606/198 |
| 5,733,325 A * | 3/1998 | Robinson et al. | 623/1.11 |
| 5,746,745 A | 5/1998 | Abele et al. | |
| 5,762,631 A | 6/1998 | Klein | 604/171 |
| 5,772,669 A | 6/1998 | Vrba | |
| 5,776,142 A | 7/1998 | Gunderson | |

(Continued)

FOREIGN PATENT DOCUMENTS

EP 0819411 1/1998

(Continued)

OTHER PUBLICATIONS

Schetsky, L., "Shape Memory Alloys", Encyclopedia of Chemical Technology (3rd ed.), John Wiley & Sons, 1982, vol. 20, pp. 726-736.

(Continued)

*Primary Examiner*—Kevin T. Truong
(74) *Attorney, Agent, or Firm*—Crompton, Seager & Tufte, LLC (57) ABSTRACT

A method and apparatus for reducing the longitudinal aspect of the catheter to stent force comprises at least one grip member for use with a stent delivery system. The grip engages a stent in the unexpanded state prior to delivery of the stent by retracting a stent retaining sheath. The grip comprises a body region having an outer diameter, a first end and a second end. The outer diameter of the first end is greater than the outer diameter of the second end. The grip is at least partially constructed from a polymeric material.

16 Claims, 4 Drawing Sheets

U.S. PATENT DOCUMENTS

| | | | |
|---|---|---|---|
| 5,817,102 | A | 10/1998 | Johnson et al. |
| 5,836,965 | A | 11/1998 | Jendersee et al. |
| 5,913,871 | A | 6/1999 | Werneth et al. |
| 5,935,135 | A | 8/1999 | Bramfitt et al. |
| 5,941,908 | A | 8/1999 | Goldsteen et al. ............... 623/1 |
| 5,944,726 | A | 8/1999 | Blaeser et al. ............... 606/108 |
| 5,954,729 | A | 9/1999 | Bachmann et al. |
| 5,968,069 | A | 10/1999 | Dusbabek et al. ........... 606/194 |
| 5,976,155 | A | 11/1999 | Foreman et al. ............. 606/108 |
| 6,007,543 | A | 12/1999 | Ellis et al. .................... 606/108 |
| 6,007,545 | A | 12/1999 | Venturelli |
| 6,027,510 | A * | 2/2000 | Alt ............................... 606/194 |
| 6,051,001 | A | 4/2000 | Borghi |
| 6,053,943 | A | 4/2000 | Edwin et al. ................. 623/1.25 |
| 6,066,169 | A | 5/2000 | McGuinness .............. 623/1.16 |
| 6,077,273 | A | 6/2000 | Euteneuer et al. ........... 606/108 |
| 6,077,295 | A | 6/2000 | Limon et al. |
| 6,077,297 | A | 6/2000 | Robinson et al. |
| 6,106,530 | A | 8/2000 | Harada ........................ 606/108 |
| 6,110,180 | A | 8/2000 | Foreman et al. ............. 606/108 |
| 6,120,522 | A | 9/2000 | Vrba et al. .................. 606/190 |
| 6,123,712 | A | 9/2000 | Di Caprio et al. ........... 606/108 |
| 6,126,685 | A | 10/2000 | Lenker |
| 6,149,996 | A | 11/2000 | Helgerson et al. |
| 6,159,227 | A | 12/2000 | Di Caprio et al. ........... 606/192 |
| 6,168,616 | B1 | 1/2001 | Brown |
| 6,168,617 | B1 | 1/2001 | Blaeser et al. ............... 623/1.11 |
| 6,203,558 | B1 | 3/2001 | Dusbabek et al. ........... 606/198 |
| 6,214,036 | B1 | 4/2001 | Letendre et al. |
| 6,228,110 | B1 | 5/2001 | Munsinger |
| 6,254,632 | B1 | 7/2001 | Wu et al. ..................... 623/1.15 |
| 6,258,099 | B1 | 7/2001 | Mareiro et al. .............. 606/108 |
| 6,264,683 | B1 | 7/2001 | Stack et al. ................. 623/1.11 |
| 6,280,412 | B1 | 8/2001 | Pederson et al. |
| 6,296,660 | B1 | 10/2001 | Roberts et al. ............. 623/1.11 |
| 6,302,906 | B1 | 10/2001 | Goicoechea et al. ....... 623/1.11 |
| 6,309,402 | B1 | 10/2001 | Jendersee et al. |
| 6,322,586 | B1 | 11/2001 | Monroe et al. |
| 6,325,814 | B1 | 12/2001 | Euteneuer et al. ........... 606/198 |
| 6,331,188 | B1 | 12/2001 | Lau et al. .................... 623/1.13 |
| 6,350,277 | B1 | 2/2002 | Kocur ........................ 623/1.11 |
| 6,371,962 | B1 | 4/2002 | Ellis et al. .................... 606/108 |
| 6,375,676 | B1 | 4/2002 | Cox ............................ 623/1.16 |
| 6,380,457 | B1 | 4/2002 | Yurek et al. |
| 6,391,032 | B2 | 5/2002 | Blaeser et al. ............... 606/108 |
| 6,391,050 | B1 | 5/2002 | Broome ...................... 623/1.11 |
| 6,391,051 | B2 | 5/2002 | Sullivan et al. |
| 6,395,008 | B1 | 5/2002 | Ellis et al. .................... 606/108 |
| 6,395,017 | B1 | 5/2002 | Dwyer et al. |
| 6,419,685 | B2 | 7/2002 | Di Caprio et al. ........... 606/192 |
| 6,428,566 | B1 | 8/2002 | Holt ............................ 623/1.11 |
| 6,443,979 | B1 | 9/2002 | Stalker et al. ............... 623/1.11 |
| 6,468,298 | B1 | 10/2002 | Pelton ........................ 623/1.11 |
| 6,468,299 | B2 | 10/2002 | Stack et al. ................. 623/1.11 |
| 6,494,906 | B1 | 12/2002 | Owens ....................... 623/1.11 |
| 6,506,201 | B2 | 1/2003 | Di Caprio et al. ........... 606/192 |
| 6,517,547 | B1 | 2/2003 | Feeser et al. ................. 606/108 |
| 6,517,570 | B1 | 2/2003 | Lau et al. .................... 623/1.13 |
| 6,569,192 | B1 | 5/2003 | Svensson et al. |
| 6,607,551 | B1 | 8/2003 | Sullivan et al. |
| 6,620,191 | B1 | 9/2003 | Svenson |
| 6,623,518 | B2 | 9/2003 | Thompson et al. |
| 6,660,031 | B2 | 12/2003 | Tran et al. |
| 6,676,667 | B2 | 1/2004 | Mareiro et al. |
| 6,682,553 | B1 | 1/2004 | Webler, Jr. |
| 6,699,274 | B2 * | 3/2004 | Stinson ...................... 623/1.12 |
| 6,814,746 | B2 * | 11/2004 | Thompson et al. ......... 623/1.11 |
| 6,890,337 | B2 | 5/2005 | Feeser et al. |
| 6,896,180 | B2 | 5/2005 | Miodunski et al. |
| 6,960,227 | B2 | 11/2005 | Jones et al. |
| 7,001,422 | B2 | 2/2006 | Escamilla et al. |
| 7,152,605 | B2 | 12/2006 | Khairkhahan et al. |
| 2001/0007082 | A1 | 7/2001 | Dusbabek et al. .......... 623/1.11 |
| 2002/0055767 | A1 | 5/2002 | Forde et al. |
| 2002/0095204 | A1 | 7/2002 | Thompson et al. |
| 2002/0099435 | A1 | 7/2002 | Stinson |
| 2002/0120321 | A1 | 8/2002 | Gunderson et al. |
| 2002/0120322 | A1 | 8/2002 | Thompson et al. |
| 2002/0120323 | A1 | 8/2002 | Thompson et al. |
| 2002/0123794 | A1 | 9/2002 | Ellis et al. ................... 623/1.15 |
| 2002/0138081 | A1 | 9/2002 | Blaeser et al. ............... 606/108 |
| 2002/0049466 | A1 | 10/2002 | Euteneuer et al. ........... 606/198 |
| 2002/0144757 | A1 | 10/2002 | Craig et al. |
| 2002/0151955 | A1 | 10/2002 | Tran et al. |
| 2002/0156519 | A1 | 10/2002 | Di Caprio et al. ........... 623/1.11 |
| 2003/0018380 | A1 | 1/2003 | Craig et al. |
| 2003/0077200 | A1 | 4/2003 | Craig et al. |
| 2003/0114912 | A1 | 6/2003 | Sequin et al. |
| 2003/0212451 | A1 | 11/2003 | Cox et al. |
| 2004/0084523 | A1 | 5/2004 | Miodunski et al. |
| 2004/0204749 | A1 | 10/2004 | Gunderson |

FOREIGN PATENT DOCUMENTS

| | | |
|---|---|---|
| EP | 1157673 | 11/2001 |
| EP | 1369098 | 10/2003 |
| WO | 93/22986 | 11/1993 |
| WO | 94/15549 | 7/1994 |
| WO | 98/07390 | 2/1998 |
| WO | WO00/71058 | 11/2000 |
| WO | 02/32496 | 4/2002 |
| WO | WO02/41805 | 5/2002 |
| WO | 02/47582 | 6/2002 |

OTHER PUBLICATIONS

U.S. Appl. No. 08/697,453, filed Aug. 23, 1996, Louis Ellis, Andy Dusbabek.

U.S. Appl. No. 10/697,453, filed Jan. 14, 2003, Fernando Dicaprio et al.

International Search Report, PCT/US2004/011023, Oct. 11, 2004.

* cited by examiner

STENT DELIVERY SYSTEM WITH SECUREMENT AND DEPLOYMENT ACCURACY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The use of stents, and other implantable medical devices such as grafts, stent-grafts, vena cava filters, etc, hereinafter referred to cumulatively as stents, to maintain the patency of bodily lumens is well known.

Stents are typically delivered via a catheter in an unexpanded configuration to a desired bodily location. Once at the desired bodily location, the stent is expanded and implanted in the bodily lumen.

Typically, a stent will have an unexpanded (closed) diameter for placement and an expanded (opened) diameter after placement in the vessel or the duct. Some stents are self-expanding; some stents are expanded mechanically with radial outward force from within the stent, as by inflation of a balloon; and some stents, known as hybrid stents, have one or more characteristics common to both self-expanding and mechanically expandable stents.

An example of a mechanically expandable stent and associated delivery system is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Self-expanding stents are constructed from a wide variety of materials including nitinol, spring steel, shape-memory polymers, etc.

In many stent delivery systems, particularly those used to deliver a self-expanding stent, the stent is typically retained on the catheter via a retention device such as a sheath. The stent may be deployed by retracting the sheath from over the stent. To prevent the stent from being drawn longitudinally with the retracting sheath, many delivery systems provide the catheter shaft with one or more bumpers or hubs.

However it is known that in many cases when a sheath is withdrawn from a stent, particularly a self-expanding stent constructed of shape memory material, the stent may be displaced longitudinally relative to the catheter shaft as a result of so-called "stent jumping," wherein when a sleeve or sheath is withdrawn from the stent during delivery the stent frictional forces and stent constrainment forces exerted by the retracting sleeve on the stent are less than those of the stent expansion force at an angle exiting the stent delivery system. As a result, in some instances, as the sheath is withdrawn from about the stent, the stent will tend to migrate or "jump" longitudinally relative to the stent mounting region of the catheter resulting in the imprecise delivery of the stent and/or distortion of the stent body. Because a portion of the stent is already expanding beyond the diameter of the catheter when stent jumping typically occurs, the presence of one or more hubs on the catheter shaft will typically not prevent stent jumping.

It would thus be desirable to provide a stent delivery system and/or one or more components thereof which may reduce or eliminate occurrences of stent jumping in order to improve the accuracy of stent placement within a vessel or other body space.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to several embodiments which seek to improve the accuracy of stent placement and reduce the occurrence and severity of stent jumping.

For example, in at least one embodiment, the invention is directed to a stent delivery system that reduces the potential for stent jumping by providing one or more protrusions to which the stent, or one or more portions thereof, may be temporarily engaged during retraction of a stent retaining sleeve or sheath. The protrusions do not interfere with the radial expansion of the stent but will prevent the stent from moving longitudinally relative to the catheter.

In some embodiments, the invention is directed to one or more bands or collars, that may be disposed about the catheter under the stent. Bands may be provided with a variety of surface features such as bumps, flaps, tabs, fins or other protrusions or surface features, against or about which a portion of the stent may be temporarily engaged. In at least one embodiment the bands are radiopaque. In some embodiments the a band is positioned adjacent to or at least partially under an end of the stent to allow the surface features of the band to engage the end affects of the stent while the remaining portion of the stent is freed to expand. In at least one embodiment, a stent is provided with one or more end regions which define a relatively large opening or gap in the stent structure to engage the surface features of an engagement band catheter shaft.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
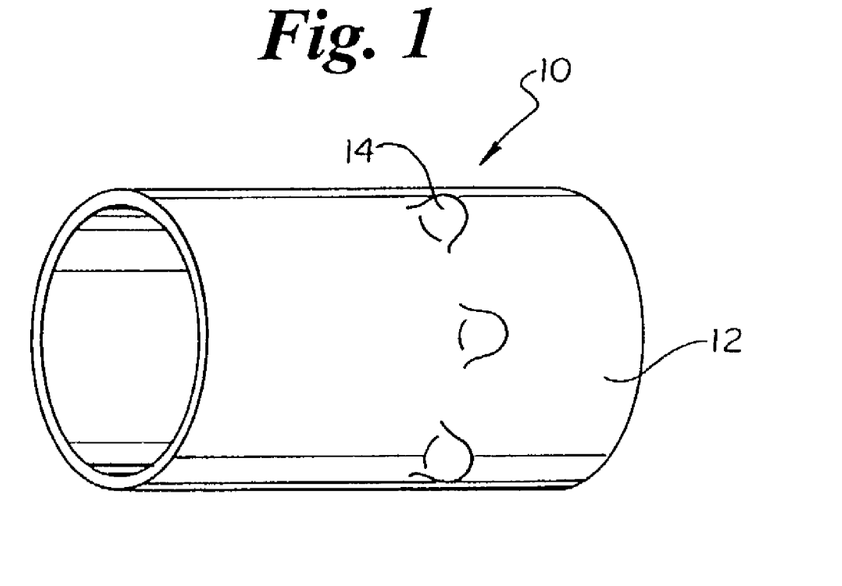
FIG. 1 is a perspective view of an embodiment of the invention.
Figure 2:
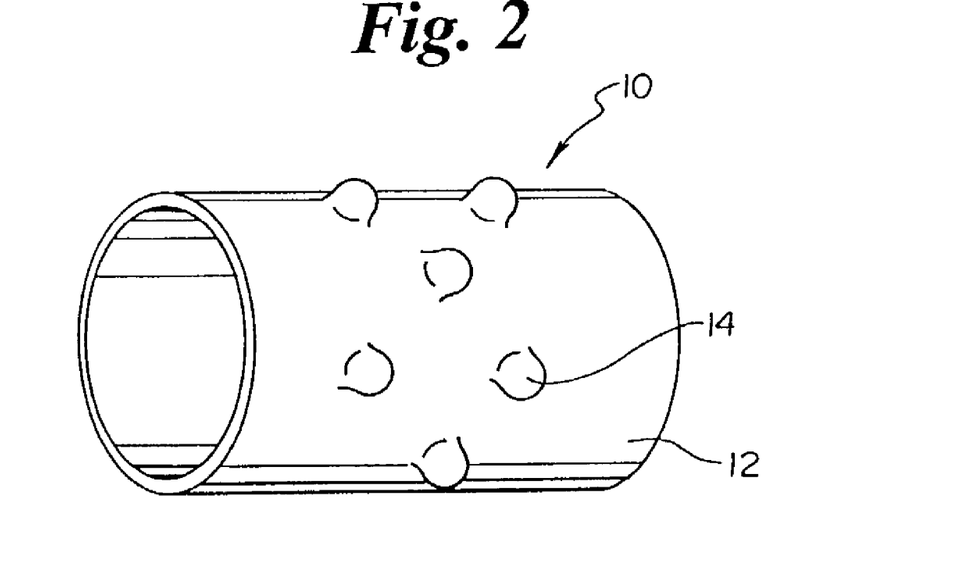
FIG. 2 is a perspective view of the embodiment shown in FIG. 1 wherein the band defines an alternative pattern of surface features.

As mentioned above the present invention is embodied in a variety of forms. For example, in the embodiment shown in FIG. 1 the invention is embodied in a stent retaining band or collar, indicated generally at 10, which has an outer surface 12 comprising one or more protrusions 14. As illustrated by FIGS. 1 and 2 the protrusions 14 may have similar or differing dimensions and orientations relative to one another. In addition, the protrusions 14 may be arranged or positioned on the outer surface 12 by columns, rows, or any other pattern desired.

Figure 3:
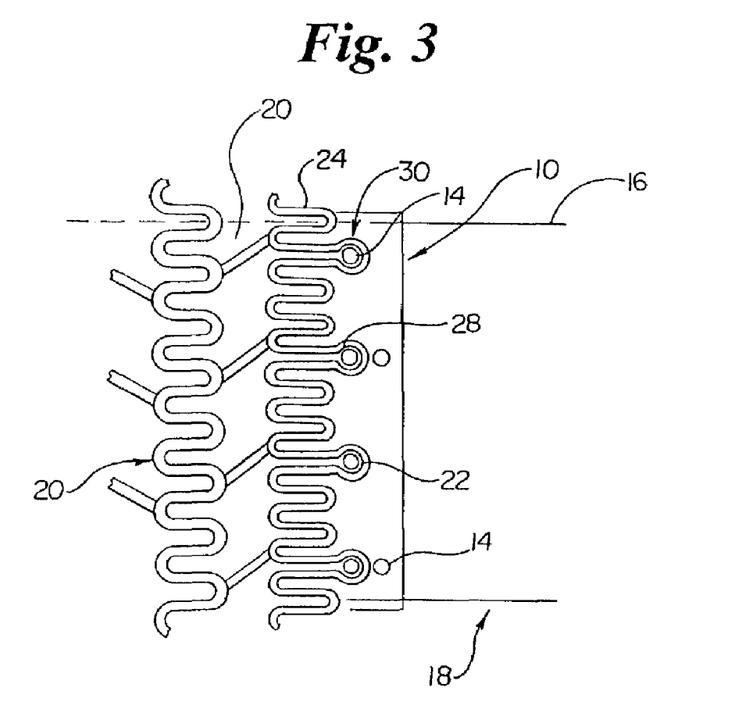
FIG. 3 is a partial side view of a stent retaining region of a stent delivery catheter with the band of FIG. 1 positioned thereon and engaged to a portion of a stent.

As is shown in FIG. 3, the pattern of protrusions 14 is determined, at least in part, based on the geometry of the stent 26 to which the protrusions 14 are designed to engage. As is shown, band 10 is constructed and arranged to be mounted on the shaft 16 of a catheter 18. The band is positioned on a stent retaining portion 20 of the shaft 16. Typically the band 10 is positioned such that one or more of the protrusions 14 pass at least partially through one or more of the openings 22 defined by the tubular wall 24 of a stent, stent-graft, graft, filter or other implantable medical device, hereinafter referred to collectively as a stent 26 or stents.

A band 10 may be positioned underneath one or both ends 30 of the stent 26, or any other portion of the stent desired. In some embodiments the band 10 may have a length equal to or greater than the length of the stent 26.

The protrusions 14 extend at least partially through the openings 22 to engage the portions or struts 28 of the stent 26 immediately adjacent thereto. In addition to, or as an alternative to positioning the protrusions 14 through one or more of the stent openings 22, in some embodiments the protrusions 14 may be positioned adjacent to one or both of the ends 30 of the stent 26.

In some embodiments of the invention, a stent 26 is provided with ends 30 whose struts 28 have been constructed to provide openings 22 which are enlarged or otherwise modified in order to more readily accommodate the positioning of the protrusions 14 therein.

In the various embodiments shown and described herein, the band 10 may be at least partially radiopaque so that the band 10 may be utilized as a marker band on a stent delivery catheter 18 such as is shown in FIGS. 3 and 8-10.

Band 10 may be constructed of a wide variety of materials including but not limited to metals, plastic, rubber, silicone, polymers, etc. Where the band 10 is at least partially constructed of metal, in at least one embodiment the metal is a radiopaque metal such as platinum, gold, iridium, etc. In at least on embodiment the metal is a biocompatible metal such as including but not limited to stainless steel, nitinol, cobalt and alloys thereof. Some polymer materials suitable for use in construction of the band 10 include one or more polyetheramide block copolymers, such as the ester linked polyetheramides sold under the trade mark PEBAX®; polyetherester block copolymer such as sold under the ARNITEL® and HYTREL®; nylon, polyethylene, etc.

The protrusions 14 may be constructed of the same or different material as the rest of the band or band body 15.

Figure 4:
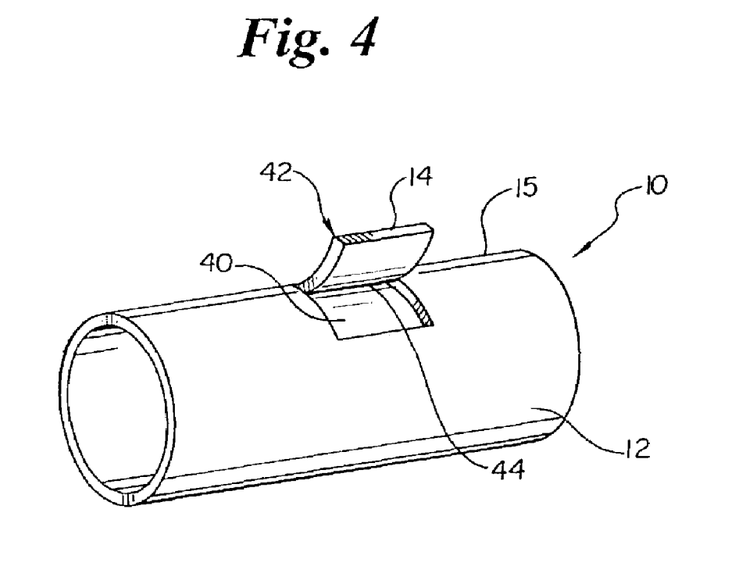
FIG. 4 is a perspective view of the band of FIG. 1 wherein the surface features are provided by cutting and folding selected portions of the band.

As indicated above the protrusions 14 may be of any shape or configuration. For example in the embodiments shown in FIGS. 1-2 the protrusions are raised portions or bumps on the surface 12 of the band and may be formed by a variety of forming mechanisms including for example molding the band and protrusions into the shape shown. In some embodiments the protrusions 14 may be made from altering the inner shaft 16 to homogeneous with the material of the band 10. Protrusions 14 may also be separate elements which are welded, stamped, punched, adhesively engaged, injection molded, melted or otherwise positioned and/or engaged onto the surface 12 of the band 10. However, as is shown in FIG. 4, protrusions 14 may also be formed by cutting out one or more openings 40 into the band 10. The material or flap 42 cut from the tube 10 remains integral and engaged to the tube 10 along at least one line or point of engagement 44. The resulting flap 42 of tube material is oriented to extend at least partially outward from the tube surface 12 to act as a protrusion 14. Where multiple flaps 42 are provided for, flaps 42 may be of any shape desired and may be of a uniform or different configuration relative to one another.

Figure 5:
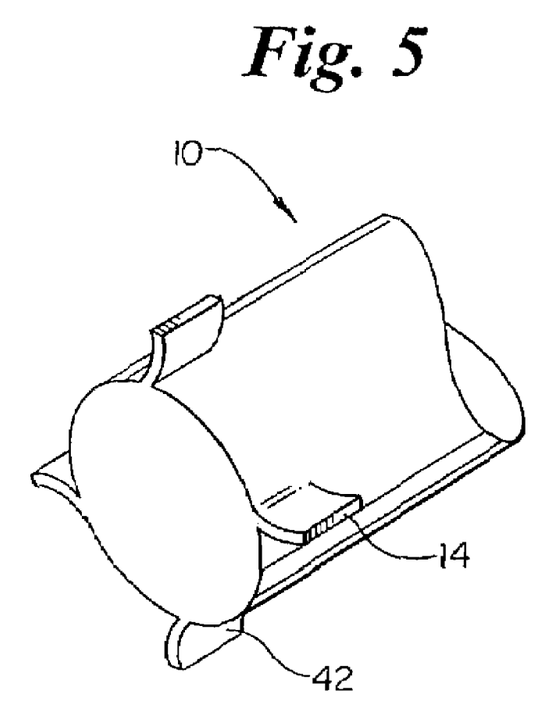
FIG. 5 is a perspective view of the embodiment of FIG. 1 wherein the surface features are tabs.

Alternatively, the band 10 may be provided with one or more flaps 42 to act as protrusions 14 without cutting or otherwise providing the band 10 with openings flaps or slots 40 from the band 10 by molding or otherwise shaping the band 10 to include flap style protrusions 14 such as are shown in FIG. 5.

Figure 6:
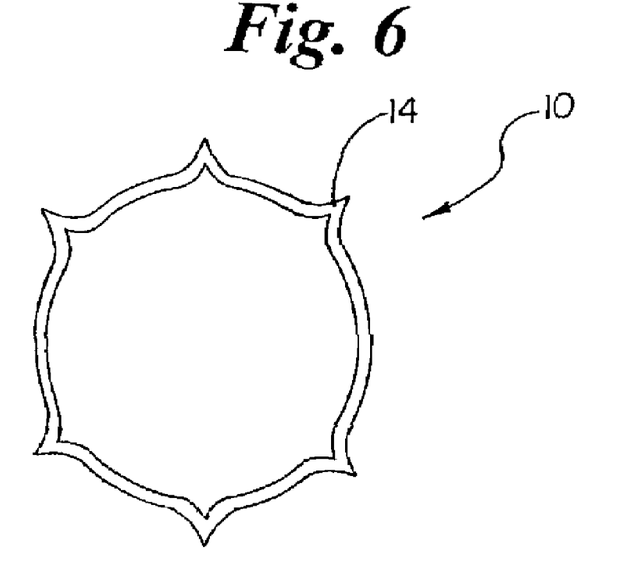
FIG. 6 is a cross-sectional view of the embodiment of FIG. 1 wherein the surface features are substantially fin shaped.

As a result of the plastic or deformable nature of the material of the band 10, in some cases one or more protrusions 14 may be provided by pinching and or pulling selected portions of the band 10 together and radially outward in order to form one or more substantially fin shaped protrusions 14 such as is shown in FIG. 6. A band 10 may be provided with substantially fin shaped protrusions by manipulating a band 10 in the manner described or by molding or other wise forming the tube 10 with the protrusions already in place.

Figure 7:
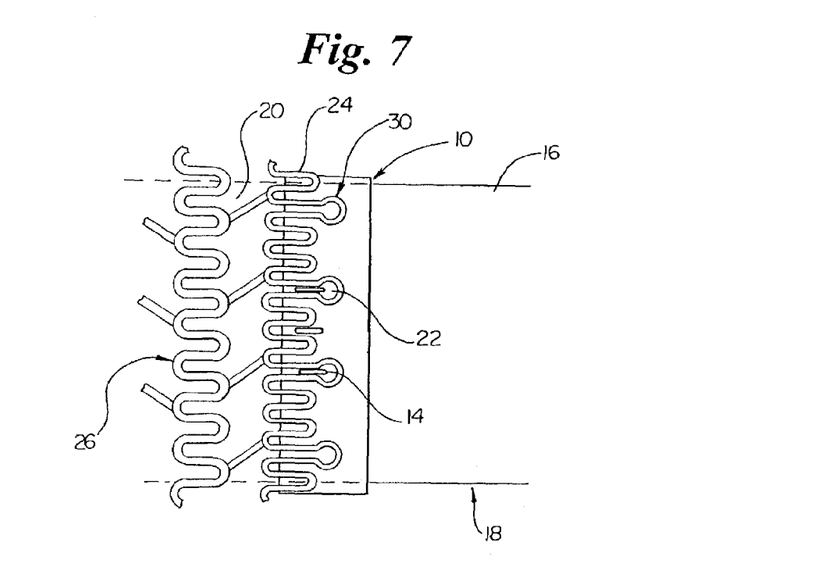
FIG. 7 is a partial side view of the embodiment shown in FIG. 2 wherein at least a portion of the stent defines an enlarged opening for engaging the band.

As indicated above, the shape, size and arrangement of the protrusions of the band are selected in order to temporarily engage at least a portion of a stent when the stent is engaged to the stent retaining area 20 of a delivery catheter. As is shown in FIG. 7, where the band 10 employs flap, fin or other somewhat elongated protrusions 14, the protrusions are designed to be positioned within the spaces or openings 22 between adjacent struts 28 of the stent 26.

Figure 8:
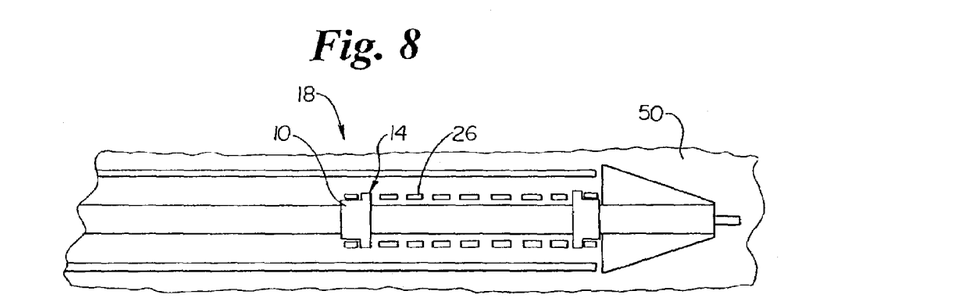
FIG. 8 is a cross-sectional side view of an embodiment of the invention.

When a stent delivery catheter 18, such as is shown in FIG. 8 being advanced through a vessel 50, is equipped with one or more bands 10, the one or more protrusions 14 of the bands 10 will engage the stent 26 in the manner described above.

Figure 9:
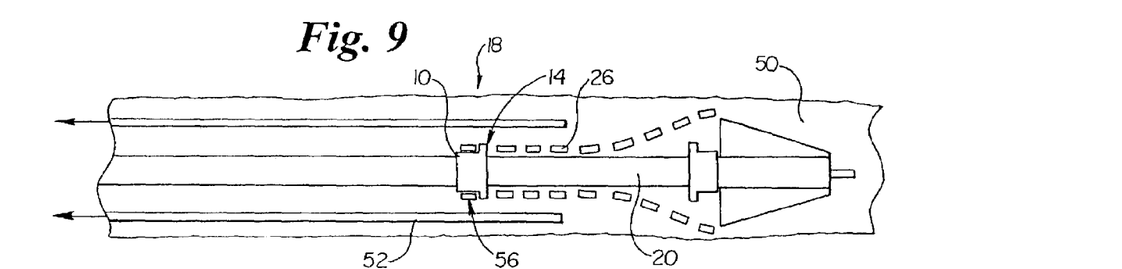
FIG. 9 is a cross sectional side view of the embodiment of FIG. 8 shown during stent delivery.
Figure 10:
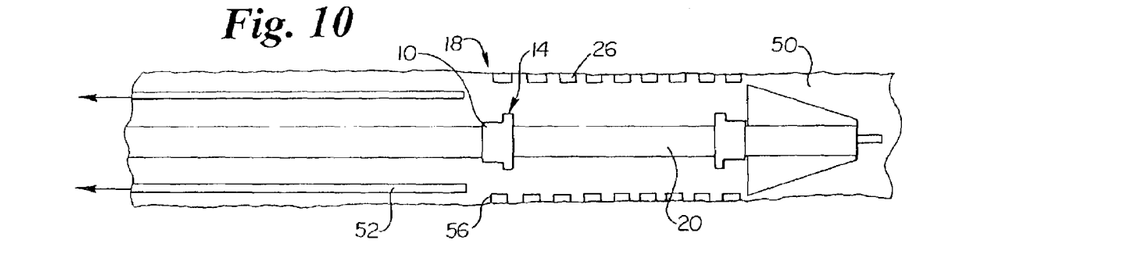
FIG. 10 is a cross sectional side view of the embodiment of FIGS. 8 and 9 shown after the stent is fully deployed.

As is shown in FIG. 9, when the catheter 18 has been positioned within the vessel 50 at a desired location, the stent retaining sheath 52 is retracted from the stent retaining area 20 to expose the stent 26 for delivery. In the embodiment shown, the protrusions 14 on the band 10 positioned adjacent to the distal end 56 of the stent 26, will continue to engage the stent 26 until the sleeve 52 is fully retracted off of the stent 26, such as is shown in FIG. 10. As a result of the engagement between the protrusions 14 and the stent 26, the band 10 acts to anchor the stent 26 to the shaft 16 thereby preventing longitudinal jump of the stent 26 relative to the catheter 18. Thus the stent 26 is deployed from the catheter 18 and into the intended area of the vessel 50 with improved precision and reliability.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent delivery system comprising:
    a catheter having an inner shaft, at least a portion of the inner shaft defining a stent mounting region;
    a stent being defined by a stent wall having a proximal region with an opening and a distal region with an opening, the stent having an unexpanded state and an expanded state, in the unexpanded state, the stent being disposed about at least a portion of the stent mounting region;
    a proximal band disposed about a proximal portion of the inner shaft, and a distal band disposed about a distal portion of the inner shaft, the proximal band and the distal band each comprising a body region having an outer surface and a protrusion extending radially outward from the other surface, when the stent is in the unexpanded state, the protrusion of the proximal band extends into the proximal opening of the stent and the protrusion of the distal band extends into the distal opening of the stent; and
    a retractable sheath overlying the stent when the stent is in the unexpanded state.

2. The stent delivery system of claim 1 wherein at least a portion of the distal band is radiopaque.

3. The stent delivery system of claim 1 wherein the stent is a self-expanding stent.

4. The stent delivery system of claim 1, wherein the stent is retained in the unexpanded state by the retractable sheath.

5. The stent delivery system of claim 1 wherein each of the protrusions is a bump on the outer surfaces of the proximal and distal bands.

6. The stent delivery system of claim 1 wherein each of the plurality of protrusions is a flap extending from the outer surface of the band.

7. The stent delivery system of claim 6 wherein each flap is constructed by forming an opening body region of the band, each flap being engaged to at least one point on the outer surface of the band adjacent to the opening from which the flap was formed.

8. The stent delivery system of claim 1 wherein at least one of the plurality of protrusions is substantially fin shaped.

9. The stent delivery system of claim 8 wherein the at least one substantially fin shaped protrusion is formed by pulling at least a portion of the outer surface of the band in a radially outward direction.

10. The stent delivery system of claim 1 wherein at least a portion of each of the bands is formed by extrusion.

11. The stent delivery system of claim 1 wherein at least a portion of each of the proximal and distal bands is formed by injection molding.

12. The stent delivery system of claim 1 wherein each of the proximal band and the distal bands is integral with the inner shaft.

13. The stent delivery system of claim 1, wherein when the retractable sheath can be retracted from the stent so that the stent expands to the expanded state, and until the retractable sheath is completely retracted off of the stent, the stent remains engaged to at least one of the plurality of protrusions.

14. The stent delivery system of claim 1, wherein the at least one band comprises one or more metals.

15. A stent delivery system comprising:
    a catheter, the catheter having an inner shaft and a retractable sheath, the inner shaft having a proximal band and a distal band engaged thereto, the proximal band and the distal band each comprising a body region having an outer surface and a protrusion extending radially outward from the outer surface; and
    a stent, at least a portion of the stent being disposed about a portion of the inner shaft, the stent having a proximal opening and a distal opening, the stent being expandable from an unexpanded state to an expanded state, in the unexpanded state, the protrusion of the proximal band extends into the proximal opening and the protrusion of the distal band extends into the distal opening, and in the unexpanded state, the retractable sheath overlies the stent.

16. A method of preventing longitudinal movement of a stent being delivered from a delivery catheter comprising a catheter shaft, a retractable sheath, a stent expandable from an unexpanded state to an expanded state, and at least one band disposed about a region of the catheter shaft underlying at least a portion of the stent, the at least one band having a proximal protrusion and a distal protrusion, the proximal and distal protrusions extending radially outward so that, in the unexpanded state of the stent, the proximal protrusion extends into a proximal opening in the stent and the distal protrusion extends into a distal opening in the stent, the method comprising moving the retractable sheath proximally so that the distal protrusion does not extend into the distal opening while the proximal protrusion remains extending into the proximal opening.

* * * * *

UNITED STATES PATENT AND TRADEMARK OFFICE
CERTIFICATE OF CORRECTION

PATENT NO. : 7,473,271 B2
APPLICATION NO. : 10/411645
DATED : January 6, 2009
INVENTOR(S) : Richard Gunderson Page 1 of 2

It is certified that error appears in the above-identified patent and that said Letters Patent is hereby corrected as shown below:

Column 6
Line 2, delete "other", and insert therefor -- outer --.
Line 22, after "an opening" and before "body region", insert -- in the --.
Line 40, delete "when".

Line 44, between "to" and "the", delete "at least one of".
Line 44, after "the", delete "plurality of protrusions", and insert therefor -- protrusions of the proximal band --.

Line 45, after "wherein the", delete "at", and insert therefor -- proximal band and the distal --.

Line 46, before "band", delete "least one".
Line 46, between "band" and "comprises", insert therefor -- each --.

Line 66, between "and" and "band", delete "at least one", and insert therefor -- a proximal band and a distal --.

Column 7
Line 1, between "the" and "band", delete "at least one", insert therefor -- proximal band and the distal --.
Line 1, between "band" and "having a", insert therefor -- each --.

Line 2, delete "proximal protrusion and a distal".
Line 2, delete ", the proximal and".

Line 3, before "extending radially", delete "distal protrusions".

Line 4, between "the" and "protrusion", delete "proximal".

Signed and Sealed this

Twentieth Day of July, 2010

David J. Kappos
*Director of the United States Patent and Trademark Office*

Column 7
Line 5, before "extends into", insert therefor -- of the proximal band --.
Line 5, after "and the", delete "distal".

Line 6, after "protrusion", insert therefor -- of the distal band --.

Column 8
Line 2, between "the" and "protrusion", delete "distal".
Line 2, after "protrusion", insert therefor -- of the distal band --.

Line 3, between "the" and "protrusion", delete "proximal".
Line 3, after "protrusion", insert therefor -- of the proximal band --.